(12) United States Patent
Browning et al.

(10) Patent No.: US 7,099,713 B2
(45) Date of Patent: Aug. 29, 2006

(54) SKIN CONDUCTION AND TRANSPORT SYSTEMS

(75) Inventors: James D. Browning, Columbus, OH (US); Vincent McGinniss, Sunbury, OH (US); Steven M. Risser, Reynoldsburg, OH (US); Dale L. Robinson, Powell, OH (US); Robert E. Russell, III, Newark, OH (US); Robert R. Boyd, Dublin, OH (US); Matthew S. Fleming, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 84 days.

(21) Appl. No.: 10/608,579

(22) Filed: Jun. 27, 2003

(65) Prior Publication Data

US 2004/0023849 A1    Feb. 5, 2004

Related U.S. Application Data

(60) Provisional application No. 60/393,036, filed on Jun. 28, 2002.

(51) Int. Cl.
*A61B 5/04*    (2006.01)
*A61B 18/14*   (2006.01)

(52) U.S. Cl. .................. 600/395; 600/397; 606/32; 604/20; 607/153

(58) Field of Classification Search ........ 600/395–397; 606/32; 607/153; 604/20
See application file for complete search history.

(56) References Cited

U.S. PATENT DOCUMENTS

| 3,027,333 | A | * | 3/1962 | Friedman ............... 600/372 |
| 4,229,479 | A |   | 10/1980 | Brick et al. |
| 4,379,454 | A |   | 4/1983 | Campbell et al. |
| 4,457,748 | A |   | 7/1984 | Lattin et al. |
| 4,458,686 | A |   | 7/1984 | Clark, Jr. |
| 4,473,492 | A | * | 9/1984 | Schmolka .................. 607/153 |
| 4,699,146 | A | * | 10/1987 | Sieverding ................ 600/391 |
| 4,705,682 | A |   | 11/1987 | Moeller et al. |
| 4,777,954 | A |   | 10/1988 | Keusch et al. |
| 4,821,733 | A |   | 4/1989 | Peck |
| 4,975,441 | A |   | 12/1990 | Gibson |
| 5,023,085 | A |   | 6/1991 | Francoeur et al. |
| 5,036,861 | A |   | 8/1991 | Sembrowich et al. |
| 5,076,273 | A |   | 12/1991 | Schoendorfer et al. |

(Continued)

FOREIGN PATENT DOCUMENTS

EP    0 295 092 A2    12/1988

(Continued)

OTHER PUBLICATIONS

Barry, B.W.; Novel Mechanisms and Devices to Enable Successful Transdermal Drug Delivery; European Journal of Pharmaceutical Sciences 14 (2); 2001; pp. 101-114; Elsevier.

(Continued)

*Primary Examiner*—Lee S. Cohen
(74) *Attorney, Agent, or Firm*—Klaus H. Wiesmann (57) ABSTRACT

Surfactants useful for enhancing the electrical conduction of electrodes attached to the surface of a patient. The surfactants are also useful in transport of materials in and out of the body of a patient (animal or human) and in the measurement of disease states. Typical surfactants particularly useful in the invention are broadly represented by protein/fatty acid based compounds. The protein/fatty acid compounds may be lipopolypeptides. In some embodiments the lipopolypeptides may be acyl peptides. Typical acyl peptides are Lamepon S™, MayTein C™ and MayTein CT™.

48 Claims, 2 Drawing Sheets

U.S. PATENT DOCUMENTS

| | | | |
|---|---|---|---|
| 5,135,480 A | 8/1992 | Bannon et al. | |
| 5,139,023 A | 8/1992 | Stanley et al. | |
| 5,140,985 A | 8/1992 | Schroeder et al. | |
| 5,143,071 A | 9/1992 | Keusch et al. | |
| 5,203,327 A | 4/1993 | Schoendorfer et al. | |
| 5,279,543 A | 1/1994 | Glikfeld et al. | |
| 5,291,887 A | 3/1994 | Stanley et al. | |
| 5,302,172 A | 4/1994 | Sage et al. | |
| 5,334,138 A | 8/1994 | Sage et al. | |
| 5,358,714 A | 10/1994 | Green | |
| 5,441,048 A | 8/1995 | Schoendorfer | |
| 5,443,080 A | 8/1995 | D'Angelo et al. | |
| 5,498,420 A | 3/1996 | Edgar et al. | |
| 5,603,693 A | 2/1997 | Frenkel et al. | |
| 5,636,632 A | 6/1997 | Bommannan et al. | |
| 5,668,170 A | 9/1997 | Gyory | |
| 5,686,516 A | 11/1997 | Tzur | |
| 5,693,604 A | 12/1997 | Su | |
| 5,760,096 A | 6/1998 | Thornfeldt et al. | |
| 5,800,685 A | 9/1998 | Perrault | |
| 5,874,095 A | 2/1999 | Deckner et al. | |
| 5,904,917 A * | 5/1999 | Mattai et al. | 424/59 |
| 5,921,925 A | 7/1999 | Cartmell et al. | |
| 5,952,000 A | 9/1999 | Venkateshwaran et al. | |
| 5,954,685 A | 9/1999 | Tierney | |
| 5,985,990 A * | 11/1999 | Kantner et al. | 600/391 |
| 5,993,848 A | 11/1999 | Suzuki et al. | |
| 6,180,416 B1 | 1/2001 | Kurnik et al. | |
| 6,232,366 B1 * | 5/2001 | Wang et al. | 600/391 |
| 6,233,471 B1 | 5/2001 | Berner et al. | |
| 6,251,083 B1 | 6/2001 | Yum et al. | |
| 6,297,204 B1 * | 10/2001 | Picard et al. | 510/136 |
| 6,319,913 B1 | 11/2001 | Mak et al. | |
| 2001/0016682 A1 | 8/2001 | Berner et al. | |
| 2001/0036483 A1 | 11/2001 | Luo et al. | |

FOREIGN PATENT DOCUMENTS

| | | |
|---|---|---|
| EP | 0 613 942 A1 | 9/1994 |
| EP | 0 804 155 B1 | 11/1997 |
| WO | WO 96/00110 | 1/1996 |
| WO | WO 00/01351 | 1/2000 |
| WO | WO 00/33812 | 6/2000 |

OTHER PUBLICATIONS

Berti, Jeffrey J. et al.; Transcutaneous Drug Delivery: A Practical Review; Mayo Clinic Proceedings.; Jun. 1995; vol. 70(6); pp. 581-586.

Hsu, Chang-Shan et al.; Anionic Gels as Vehicles for Electrically-Moduated Drug Delivery. 1. Solvent & Drug Transport Phenomena; Pharrmaceutical Research; vol. 13, No. 12; 1996; pp. 1865-1870.

Kanikkannan, N. et al.; Structure-activity Relationship of Chemical Penetration Enhancers in Transdermal Drug Delivery; Current Medicinal Chemistry; 2000; 7; pp. 593-608.

Panchagnula, Ramesh; Transdermal Iontophoresis Revisited; Next Generation Therapeutics; pp. 468-473.

Peck, Kendall; Flux Enhancement Effects of Ionic Surfactants Upon Passive & Electroosmotic Transdermal Transport; J. of Pharmaceutical Sciences; vol. 87; 9; Sep. 1998;pp. 1161-1169.

Sanderson, John E.; Iontophoretic Delivery of Nonpeptide Drugs: Formulation Optimization for Maximum Skin Permeability; J. of Pharmaceutical Sciences; vol. 78; No. 5; May 1989; pp. 361-364.

Vyas, S.P.; et al.; Percutnaeous Permeation: Principles, Means and Methods to Enhance the Permeation; Indian Drugs; 37(10; Oct. 2000; pp. 454-463.

Wang, Youmin et al.; Effect of Sodium Dodecyl Sulfate on Iontophoresis of Hydrocortisone Across Hairless Mouse Skin; Pharmaceutical Development & Technology; 5(4); pp. 533-542; 2000.

Xu, Ping et al.; Enhanced Skin Permeability for Transdermal Drug Delivery: Physiopathological & Physicochemical Considerations; Critical Reviews in Therapeutic Drug Carrier Systems; 8(3) pp. 211-236; 1991.

* cited by examiner

SKIN CONDUCTION AND TRANSPORT SYSTEMS

This application claims benefit of provisional application 60/393,036 filed Jun. 28, 2002.

The entire disclosure of the referenced provisional application is incorporated herein by reference as if completely rewritten herein.

FIELD OF THE INVENTION

This invention relates to materials and methods for providing enhanced mucous membrane or skin conductivity in electrical measurements involving the surface of an animal or human. The invention also provides materials and methods for enhanced transport of substances across the mucous membrane or skin boundary of an animal or human.

BACKGROUND OF THE INVENTION

The measurement of internal body conditions by means of external measurements is the preferred measurement technique for diagnosing disease or monitoring body conditions. The goal for measurement by external measurements is to be as minimally invasive as possible to achieve measurement of the desired internal condition. Many devices have been designed to achieve the above goals through the use of electrical or electrochemical surface measurements.

Another important technique that is becoming increasingly important is the transdermal administration of drugs as a preferred mode of delivery. Transdermal delivery of drugs provides many advantages over other means of administration such as oral or by injection. Advantages include safety, convenience, increased patient compliance, non-interrupted therapy, avoidance of the hepatic first pass effect, and the high degree of control of any administered drug.

Many drugs are not amenable to transdermal delivery due to the well known barrier properties of the skin. Drug molecules that are intended to penetrate into the body through intact skin must first penetrate the stratum corneum and materials therein or on its surface. The drug molecule must then penetrate viable epidermis, the papillary dermis, and then the capillary walls before entering systemic circulation. In its path into the body, each of the mentioned tissues will exhibit different resistances to penetration by the same drug molecule. It is the stratum corneum, however, that presents the greatest barrier to absorption by topical administration or transdermal administration for most molecules. Muscous membranes present similar problems depending on the materials that are desired to penetrate the membrane.

BRIEF DESCRIPTION OF THE INVENTION

Broadly, one embodiment of the invention provides for enhanced electrical contact between an electrode and a patients surface (e.g. mucous membrane, skin). Enhanced electrical contact typically provides for greater reliability of measurements for the diagnosis of body conditions. In addition, improved electrical contact typically provides for greater sensitivity, comfort and ease of use for many applications.

Broadly, another embodiment of the invention provides for enhanced transdermal or trans-mucuous membrane delivery of drugs or other materials.

Broadly, a still further embodiment of the invention provides for diagnosis of bodily conditions by transdermal or trans-mucous membrane movement of body fluids to an external detection device.

A first broad embodiment for an electrode providing electrical contact with a surface of a patient includes a conductive member; and a conduction enhancer in contact with the conductive member including a carrier and a protein/fatty acid based compound. Typically, the protein/fatty acid based compound may be a lipopolypeptide, the lipopolypeptide may be an acyl peptide, and the acyl peptide may be a material selected from the group consisting of Lamepon S™, MayTein C™, MayTein CT™, and mixtures thereof. The carrier and conduction enhancer typically provide electrical contact with an electrical resistivity of less than about 10K Ohms when the electrode is applied to the patient's surface.

Typical activities for the surfactant (conduction enhancer) according to the invention include: activity between about 0.25% and about 60%; preferably an activity between about 4% and about 50%, more preferably an activity between about 5% and about 30%; and most preferably has an activity between about 10% and about 30%.

A yet further embodiment of the invention includes a method for decreasing the electrical resistivity between an electrode and the surface of a patient including placing a carrier and a conduction enhancer of a protein/fatty acid based compound between the electrode and the surface. Typically, the method according the carrier and conduction enhancer provide electrical contact with an electrical resistivity comprising less than about 10K Ohms when the electrode is applied to the patient's surface. Typically, the electrical resistivity is obtained in about 0.001 seconds to about 3 minutes; in other embodiments the electrical resistivity is obtained within about 0.01 seconds to about 30 seconds. In yet other embodiments the electrical resistivity is less than about 6K Ohms. Typically, the electrical resistivity is maintained for at least about 8 hours, and most preferably the electrical resistivity is maintained for at least about 72 hours. Typically, the composition comprises a gelling agent.

In some embodiments, the invention provides for a composition for enhancing the electrical conductivity between an electrode and a patient's surface including: a mixture comprising a carrier and a protein/fatty acid based compound. The composition may be a lipopolypeptide, an acyl peptide and the like. Typically, the acyl peptide comprises a material selected from the group consisting of Lamepon S™, MayTein C™, MayTein CT™, and mixtures thereof. Typically, the carrier and conduction enhancer provide electrical contact with an electrical resistivity comprising less than about 10K Ohms when the electrode is applied to the patient's surface.

In further embodiments, the invention provides for an electrode providing electrical contact with a surface of a patient, the electrode comprising: a conductive member; and a conduction enhancer in contact with the conductive member comprising a carrier and a surfactant represented by the formula:

$$R'\text{—CO—NH}\{CR''H\text{—CO—NH—CRH}\}_n \text{COOM}$$

wherein R, R', and R" are the same or different and may be independently selected from the group consisting of alkyl, aryl, amine, carbonyl, and carboxyl moieties; R, and R" may also be independently selected from the group consisting of —H, and —SH;

wherein the repeat unit, n, is an integer from about 2 to about 2000; and wherein M is a metal ion. Typically, when a carbon containing moiety is selected, R, R', and R" have 1–20 carbon atoms. Typically, the repeat unit, n, is an integer from about 150 to about 1800. In some embodiments, the surfactant is a mixture of compounds selected from the formula. The metal ion, M, is typically selected from the group consisting of $K^+$, $Na^+$, and mixtures thereof.

In additional embodiments, the invention includes a method for making electrical contact between an electrode and a patient's surface, which comprises the step of applying an electrode having a surface coated with a mixture of a carrier and a conduction enhancer comprising a protein/fatty acid based compound. Typically, the patient's skin is unabraded. Some embodiments provide for conditions where the electrical resistivity is obtained in about 0.001 seconds to about 3 minutes, more preferably where the electrical resistivity is obtained within about 0.01 seconds to about 30 seconds. Most preferably the electrical resistivity is less than about 6K Ohms. The resistivity is preferably maintained for at least about 8 hours and most preferably at least about 72 hours.

In another embodiment according to the invention, there is provided a method for the noninvasive measurement of body substances from a patient including the steps of applying a multilayer patch to the skin of the patient; wherein at least one layer of the multilayer patch comprises a transdermal migration-enhancing amount of an acyl peptide; and measuring a body substance, the transdermal migration of which into the multiplayer patch is facilitated by the acyl peptide. The method may include the additional step of enhancing the migration of the body substance by reverse electro transport. In some embodiments, the reverse electro-transport comprises iontophoresis.

In yet anther embodiment of the invention, there is provided a device for measuring the quantity of a body substance in a patient comprising: a multiplayer patch device including a first layer comprising an acyl peptide; a second layer comprising a reaction layer; and a third layer comprising a readout visible to a user indicative of the level of the body substance in the patient.

A further embodiment includes a method for enhancing patient surface/electrode conduction for electrosurgery in a patient comprising: applying a conduction enhancing amount of a mixture of a carrier material and a conduction enhancer comprising a protein/fatty acid based compound.

An additional embodiment provides for a surgical electrode for electrosurgery comprising a conductor and a conduction-enhancing amount of an acyl peptide. And another embodiment provides for an electrode for electrosurgery in a patient comprising: a conductor; and a conduction-enhancing amount of a mixture of a carrier and a surfactant selected from the group consisting of Lamepon S™, MayTein C™, MayTein CT™, and mixtures thereof, wherein the mixture is applied to a surface of the conductor.

DETAILED DESCRIPTION OF THE INVENTION AND BEST MODE

Definitions

% Active—this term means that the stated percent (weight percent) of the substance is contained in the solution or gel.

%—all percent measurements are in weight percent unless stated otherwise.

Breakthrough time—the time required for the solution to be transported through the membrane(s), and contact and bridge two pieces of copper wire (wire gap~0.0625 inch).

Conductive—as used herein refers to electrical conductivity unless otherwise explicitly stated.

Non-conductive—as used herein refers to electrically non-conductivity unless otherwise explicitly stated.

Patient's surface—in one embodiment the patient's surface to which an electrode or a patch is applied is a mucous membrane while in another embodiment the patient's surface to which an electrode or patch is applied is the skin.

Broadly the invention discloses new materials and methods for the testing and evaluation of mammalian and particularly human body parameters. The parameters include electrical and chemical characteristics of the body. The present invention provides for improved conductivity between electrodes and a patient's (animal or human) mucous membrane or skin.

The materials of the present invention can be applied as liquids or gels (mixed with gelling agents). The liquid form is typically applied by absorption into foams, fibrous networks or other materials that absorb, adsorb or otherwise hold the material in place.

Typical materials useful in the invention include surfactants to enhance conductivity at the patient's surface/electrode interface. In other embodiments the materials of the invention provide enhanced drug delivery through the intact skin or mucous membranes with and without the aid of electrical current. Typically, the surfactant is a protein based surfactant having hydrophilic and hydrophobic properties, and/or lipophilic and lipophobic properties. A typical protein based surfactant is a lipopolypeptide. The lipopolypeptide is typically made from long chain fatty acids and hydrolyzed protein. The long chain fatty acids may be of animal or plant origin. The polypeptide may likewise be of animal or plant origin. Preferably the lipopolypeptide is a natural or modified coconut oil and hydrolyzed protein (typically collagen). The typical general chemical structure can be represented as follows:

R'—CO—NH {CR"H—CO—NH—CRH}$_n$ COOM

Typically, R, R', and R" are the same or different and may be selected from the group consisting of alkyl, aryl, amine, carbonyl, or carboxyl moieties; and R and R' may also be independently selected from the group consisting of —H, or —SH. In some embodiments, when a carbon containing moiety is selected, R, R', and R" typically have about 1 to about 20 carbon atoms; preferably R" typically has about 2 to about 10 carbon atoms. The value for the repeat unit, n, is typically about 2 to about 2000 and preferably about 150 to about 1800. In some embodiments, the lipopolysacharide represented by the formula is a complex mixture having various R, R', R" groups, that typically have various amounts of carbon atoms, and various values for the repeat unit, n. The ion —M is typically a metal ion (such as $K^+$, or $Na^+$, or mixtures thereof) that provides acceptable surfactant properties.

The surfactant materials are typically prepared by the reaction of the carboxyl group (—COOH) of a fatty acid with the amino group (—$NH_2$) of a polypeptide. The length of the fatty acid chain and the length of the polypeptide chain as well as the side groups are selected to provide characteristics for matching the physical and chemical properties of the surface of the patient and (e.g. skin or mucous membrane) and enhancing electrical conductivity between the patient's surface and an electrode.

In some embodiments, the surfactant materials are typically acylated polypeptide salts. The acylated polypeptide salts are typically represented by Lamepon S™, MayTein C™ and MayTein CT™. MayTein C™ is similar to Lamepon S™. MayTein CT™ has an additional R" group located at the asterisk in the above formula. M may be a $K^+$, $Na^+$, or similar ion. Lamepons and MayTeins may be obtained from Henkel Corp. They are typically condensation products of protein hydrolysates and vegetable fatty acids. Lamepon S™ is a lipopolypeptide made from natural coconut oil and hydrolized collagen.

Typically, for improved electrical conductivity, the surfactants of the present invention are provided having activities of between about 0.25% to about 70%. Preferably typical activity ranges are between about 4% and 50%. More preferably are activities between about 5% and 30%. At the lower end of the activity scale the activities are most preferably above 10%. This is because the lowest electrical resistance for the tested substances has been observed in the neighborhood of about 20%.

Test Apparatus for Artificial Skin

Figure 1:
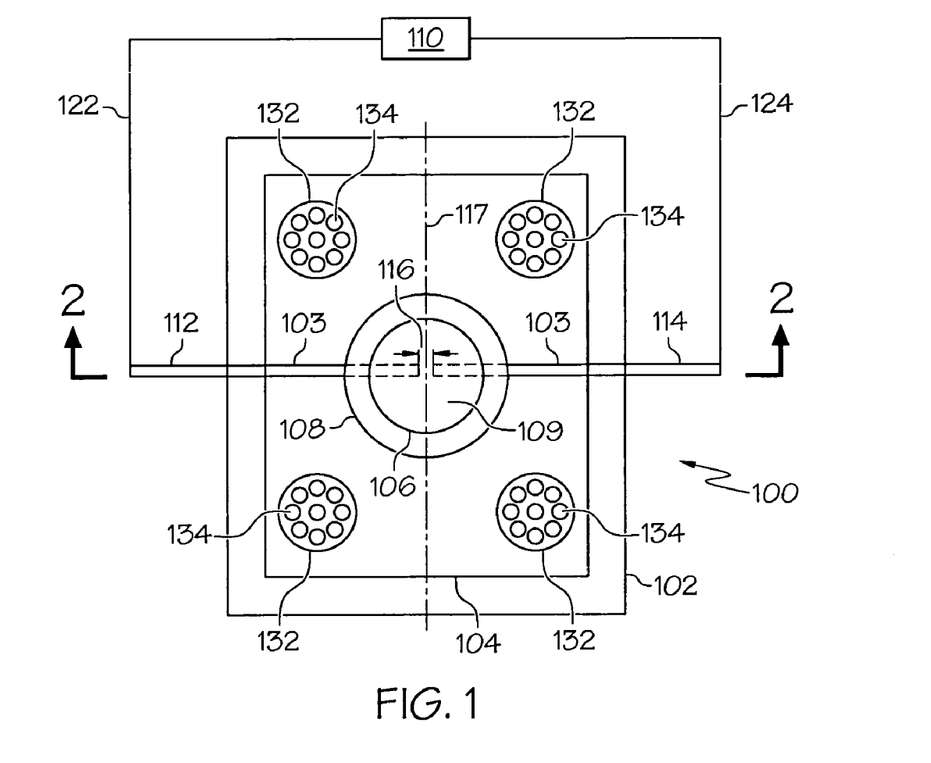
FIG. 1 is a schematic drawing of a top view of apparatus used for testing surfactant penetration of surfaces such as membranes or skin.

Referring now to FIG. 1, this figure illustrates a schematic diagram of a top view of testing apparatus 100. Apparatus 100 was used for testing surfactant penetration of several membrane types with several surfactants. A base 102 for testing apparatus 100 is typically constructed of poorly electrically conducting or electrically non-conducting material such as plastic and the like. The particular material used in the tests was Plexiglas and was about 0.125 inch thick. A groove 103 is cut into base 102 so that it went completely across the base 102. Two pieces of 20 gauge copper wire 112, 114 are inserted into groove 103 and placed such that a gap 116 of about. 1/16" is maintained between the copper wires 112, 114 at about the centerline 117 of the base 102.

A test material 108 is typically placed over the gap 116 so that it is centered thereon. A cover 104 of similar or like material as base 102 was placed over the test material. Cover 104 has a centrally placed opening 106.

When used for tests, a test material was placed so it covered the centrally placed opening. One or more drops of surfactant material were placed dropwise onto a test material its upper surface 109 and substantially in the area over gap 116.

A Fluke ohmmeter 110 (e.g. Model 89 IV True RMS Multimeter) was connected to copper wires 112, 114 via leads 122, 124 for testing artificial skin such as one or more layers of membranes represented by test material 108.

Typical test materials used with the test apparatus are layers of polycarbonate and nylon as more fully discussed in the examples below.

Figure 2:
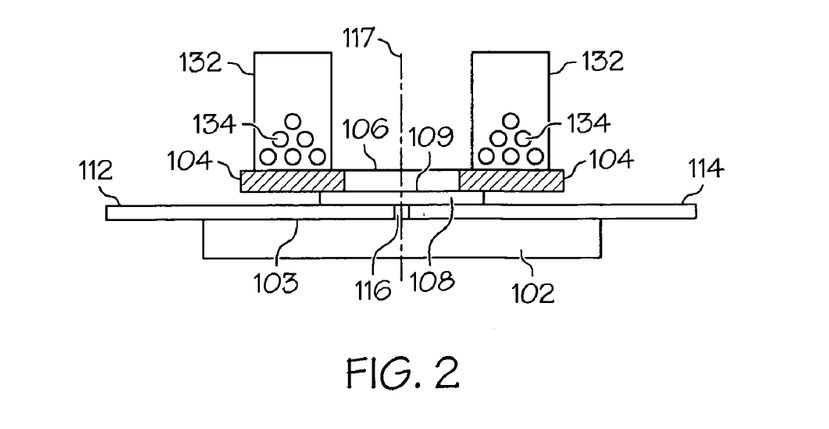
FIG. 2 is a schematic drawing of a side cutaway view of the apparatus of FIG. 1 along section 2.

Four identical 100 g weighted vials 132 containing weights 134 were placed in the corners of the cover 104 to hold the cover 104 over the test material 108. FIG. 2 as a sectional view of FIG. 1 along the plane represented by Section 2—2.

Figure 3:
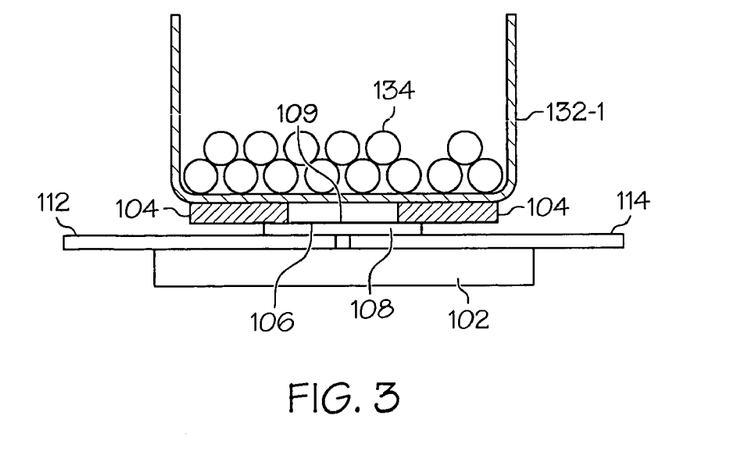
FIG. 3 is a schematic drawing of a side cutaway view of another embodiment of the apparatus for determining conductivity.

Referring now to FIG. 3, in some tests the four vials 132 for weighting were replaced by one large vial 132-1. Otherwise the materials were the same.

EXAMPLE 1

(Conductivity and Resistivity of Surfactant Solutions)

Tests were made of sixteen (16) surfactants. Fifteen of the surfactants had been diluted to an activity of 5% with deionized water. A deionized water sample EEG-16 was used as a control. One sample EEG-14, consisting of 3ML-15638 oil/water emulsion was determined to be already very diluted and so was used, as received, at 80% activity. The surfactant solutions were all mixed for 30 minutes prior to electrical conductivity testing using a VWR conductivity meter Cat# 23226–50, Probe Cat# 23226-524, range 0.1-200 u S/cm. Results are shown in Table 1.

TABLE 1

Conductivity and Resistivity of Standardized Surfactant Solutions

| Sample | Surfactant | As Received (% Active) | Surfactant grams @ 5% | Deionized Water (gram) | Surfactant solution total weight (gram) | % Active | Surfactant solution conductivity VWR (µS/cm) | Surfactant solution Resistivity (Ohm-meter) |
|---|---|---|---|---|---|---|---|---|
| EEG-1 | Actrosol C-75 ™ (clear) | 70% | 1.07 | 13.93 | 15 | 5 | 8860 | 1.1 |
| EEG-2 | Actrosol C-85 ™ (disp.) | 75% | 1.00 | 14.00 | 15 | 5 | 5300 | 1.9 |
| EEG-3 | Actrosol OY-75 ™ (disp.) | 75% | 1.00 | 14.00 | 15 | 5 | 5230 | 1.9 |
| EEG-4 | Chembetaine C ™ (disp.) | 35% | 2.14 | 12.86 | 15 | 5 | 5880 | 1.7 |
| EEG5 | Desonic DA-4 ™ (disp.) | 100% | 0.75 | 14.25 | 15 | 5 | 12.1 | 826.4 |
| EEG-6 | DeSulf SLES 301 ™ (clear) | 25% | 3.00 | 12.00 | 15 | 5 | 6880 | 1.5 |

TABLE 1-continued

Conductivity and Resistivity of Standardized Surfactant Solutions

| Sample | Surfactant | As Received (% Active) | Surfactant grams @ 5% | Deionized Water (gram) | Surfactant solution total weight (gram) | % Active | Surfactant solution conductivity VWR (μS/cm) | Surfactant solution Resistivity (Ohm-meter) |
|---|---|---|---|---|---|---|---|---|
| EEG-7 | Dodecyl Sulfate Sodium Salt (clear) | 98% | 0.77 | 14.23 | 15 | 5 | 6300 | 1.6 |
| EEG-8 | Fluorad FC-129 ™ (clear) | 50% | 1.50 | 13.50 | 15 | 5 | 4820 | 2.1 |
| EEG-9 | Lamepon S ™ (clear) | 32% | 2.34 | 12.66 | 15 | 5 | 78.3 | 127.8 |
| EEG-10 | Lodyne S-103A ™ (clear) | 45% | 1.67 | 13.33 | 15 | 5 | 4890 | 2 |
| EEG-11 | Lodyne S-222N ™ (disp.) | 85% | 0.88 | 14.12 | 15 | 5 | 211 | 47.4 |
| EEG-12 | MayTein C ™ (clear) | 36% | 2.08 | 12.92 | 15 | 5 | 9000 | 1.11 |
| EEG-13 | MayTein CT ™ (clear) | 38% | 1.97 | 13.03 | 15 | 5 | 4600 | 2.2 |
| EEG-14 | 3M L-15638 ™ (emulsion (o/w)) | 80% | 15.00 | 0.00 | 15 | 80 | 58 | 172.4 |
| EEG-15 | T-MAZ 20 Peg ™ Ester (clear) | 100% | 0.75 | 14.25 | 15 | 5 | 129.5 | 77.22 |
| EEG-16 | Deionized Water | — | 0.00 | 15.00 | 15 | — | 9.43 | 1060.4 |
| EEG-17 | High Purity Water | — | 0.00 | 15.00 | 15 | — | 1.51 | 6622.5 |

EXAMPLE 2

(Polycarbonate Skin Model)

In Example 2, tests were performed on surfactants shown in Table 2 using test apparatus 100. The test material 108 consisted of a five layer stack of polycarbonate membranes. The membrane consisted of a polycarbonate Whatman Nuclepore™ membrane having a 0.05 μm pore size (Cat. # 111703). Each had a thickness of 6 μm resulting in a stack about 30 μm thick. A Fluke Ohmmeter was used for measurement of the conductive contact time. The membrane size was cut to 0.75 in. square, and placed in the test holder, followed by addition of 400 grams of weight on the cover 104 for holding the samples in place. The opening 106 in cover 104 was ⅜" in diameter and used to make the tests shown in Table 2. Readings were made after 1 minute of contact with a drop of surfactant.

In this example, the stack of polycarbonate membranes was used to determine the ability of different surfactant solutions listed in Table 2 to penetrate the surface of the polymer artificial skin models. Breakthrough time was determined as the time required for the surfactant solution to be transported through the membrane(s) and contact and bridge two pieces of 20 gage copper wire (wire gap about 0.0625 inch).

Table 2 shows the results for fifteen surfactant systems. (5% solutions based on the active ingredients) and their penetration capabilities on polycarbonate membrane stacks. A direct comparison was also made between the surfactant solutions and deionized water as shown. The 3ML-15638 emulsion was used at 80% activity, since it was considered to already be very dilute.

TABLE 2

Initial Solution Screening Tests Through Polycarbonate Membranes (0.75" diameter).

| Sample # | Surfactant | % Active | Surfactant Breakthrough Time (sec.) |
|---|---|---|---|
| EEG-1 | Actrosol C-75 ™ (clear) | 5% | .01. |
| EEG-2 | Actrosol C-85 ™ (disp.) | 5% | .05 |
| EEG-3 | Actrosol OY-75 ™ (disp.) | 5% | .01 |
| EEG-4 | Chembetaine C ™ (disp.) | 5% | .01 |
| EEG-5 | Desonic DA-4 ™ (disp.) | 5% | 300 |
| EEG-6 | DeSulf SLES 301 ™ (clear) | 5% | 230 |
| EEG-7 | Dodecyl Sulfate Sodium Salt (clear) | 5% | 14 |
| EEG-8 | Fluorad FC-129 ™ (clear) | 5% | .06 |
| EEG-9 | Lamepon S ™ (clear) | 5% | .02 |
| EEG-10 | Lodyne S-103A ™ (clear) | 5% | .01 |
| EEG-11 | Lodyne S-222N ™ (disp.) | 5% | .03 |
| EEG-12 | MayTein C ™ (clear) | 5% | 19 |
| EEG-13 | MayTein CT (clear) | 5% | .01 |
| EEG-14 | 3ML-15638 ™ (emulsion (o/w)) | 80% | 34 |
| EEG-15 | T-MAZ 20 ™ Peg Ester (clear) | 5% | .02 |
| EEG-16 | Deionized Water | 100% | 154 |

EXAMPLE 3

After the tests in Example 2, there was a concern that the ⅜" diameter opening was too small and may allow wicking of the test material around the edges of the test material onto the copper wires. Therefore, a different cover was prepared having about a one (1) inch opening for additional tests as shown in Table 3. Results were about the same. This showed that that wicking was not a problem. However, the larger diameter opening was used in the remainder of the tests. In addition, larger test material samples were prepared that were about 1.25 inch in diameter. Except for the larger opening and larger test material sample size, test parameters were the same as in Example 2.

TABLE 3

5% Surfactant Solution Penetration Tests on 5 Layers (Total thickness = 30 μm) of Polycarbonate Membranes

| Sample # | Surfactant | % Active | Surfactant Breakthrough Time (seconds) |
|---|---|---|---|
| EEG-1 AC | Actrosol C-75 ™ (clear) | 5% | 0.01 |
| EEG-3 AY | Actrosol OY-75 ™ (disp.) | 5% | 0.01 |
| EEG-9 LS | Lamepon S ™ (clear) | 5% | 0.02 |
| EEG-12 MC | MayTein C ™ (clear) | 5% | 14.67 |
| EEG-13 MT | MayTein CT ™ (clear) | 5% | 0.10 |
| EEG-15 TM | T-Maz 20 ™ Peg Ester (clear) | 5% | 27.00 |

EXAMPLE 4

(Nylon Membrane Skin Model)

The membrane used as another polymeric model for human skin was a nylon Spectra/Mesh™ membrane having 8 μm openings with a thickness of 75 μm (Cat # 1465128). Three layers of the nylon membrane were used for a total thickness of 225 μm. The membranes were layered so that the visible directional lines apparent on the surface were oriented in different directions. One layer was oriented ↑, the lines in the second layer were oriented to the right →, and the lines in the third layer were at a 45 degree angle to these. This staggering of the layer weave was done to prevent direct lineup of any pores in the material and to make the material mimic the skin to a higher degree.

Test parameters and conditions were the same as in the previous Examples. The membrane size was cut to 1.25 in. diameter placed in test holder followed by addition of 400 grams of weight for hold down. The deionized water (EEG-16) in Table 2 required 1:32 minutes before the nylon surface even wetted.

Tests were performed for the formulations shown in Table 4 with addition of a dye so that wicking area could be evaluated. This example definitely showed that with a larger 1" opening that wicking was not a problem. The largest wicking area was 0.81 inch in diameter for Sample EEG-3 AY.

TABLE 4

Surfactant Breakthrough Time VS Water Using Three Layers (225 μm) of Nylon as the Membrane Material.

| Sample # | Surfactant | % Active | Surfactant Breakthrough Time (seconds) | Resistivity at 1 Minute Post Breakthrough (Ohm-meter) |
|---|---|---|---|---|
| EEG-1 AC | Actrosol C-75 ™ (clear) | 5% | 0.01 | N/A |
| EEG-3 AY | Actrosol OY-75 ™ (disp.) | 5% | >300 | No contact |
| EEG-9 LS | Lamepon S ™ (clear) | 5% | 0.01 | 222 K ohms |
| EEG-12 MC | MayTein C ™ (clear) | 5% | 0.01 | 1.25 M ohms |
| EEG-13 MT | MayTein CT ™ (clear) | 5% | 0.01 | 1.16 M ohms |
| EEG-15 TM | T-MAZ 20 ™ Peg Ester (clear) | 5% | 0.01 | 4.67 M ohms |
| EEG-16 | Deionized Water | 100% | >300 | No contact |

EXAMPLE 5

Tests were performed as in Example 4 except an additional layer of the. same nylon membrane was added. This time the weave of the nylon layers was staggered as follows for each layer (1)↑, (2)→, (3)↓, (4)←. Results are shown in Table 5. Sample EEG-3 AY was not tested because no contact had been made with only three layers of nylon. Results are shown in Table 5. No contact was noted for samples EEG-1 AC and EEG-15 TM. It was found that EEG-1 AC and EEG-15 TM penetrated three layers but no solution was found beyond the three layers. For comparison, all the solutions in Table 3 went though five layers of a Nuclepore polycarbonate membrane.

TABLE 5

Surfactant Break Through Time Vs Water (Total thickness 300 μm - Four Layer Nylon Membrane as Skin Model)

| Sample # | Surfactant | % Active | Surfactant Breakthrough Time (seconds) | Surfactant solution Resistivity (Ohm meter) |
|---|---|---|---|---|
| EEG-1 AC | Actrosol C-75 ™ (clear) | 5% | >300 | No contact |
| EEG-9 LS | Lamepon S ™ (clear) | 5% | 0.01 | 0.9734 M ohms |
| EEG-12 MC | MayTein C ™ (clear) | 5% | 0.01 | 2.37 M ohms |
| EEG-13 MT | MayTein CT ™ (clear) | 5% | 0.01 | 5.12 M ohms |
| EEG-15 TM | T-MAZ ™ Peg Ester (clear) | 100% | >300 | No contact |

Actrosol C-75 (EE-1 AC) penetrated through three layers, but in the fourth layer there was no solution observed. T-MAZ Peg Ester (EEG-15 TM) penetrated through three layers, but in the fourth layer there was no solution observed.

EXAMPLE 6

Human Subject Test Results

The tests were performed with Nicolet AgCl electrodes (019-417600), an impedance meter, a digital storage scope and digital voltmeter. A reference electrode and ground electrode were placed on the subject on the right side of the forehead and the shoulder respectively. Standard abrasion and 10/20 gel were used. The reference to ground measurements were verified throughout the test. Impedance was 1 k Ohm and the half-cell potential was 18–22 mV. All tests were done on the forehead with no skin preparation. All test substances were placed via a swab onto the forehead followed by the AgCl electrode held in place with medical tape. A new site and electrode was used with each test.

All solutions used were standardized to 5% activity. Maytein C™; Lamepon S™; Dodecyl Sulfate, Na salt; and Actrosol C75™ gave results better or equal to reference samples 10/10 gel, Ultrasonic gel, and Elefix™ gel.

TABLE 6

Example 6 Results

| Sample/ Substance (5% Solutions) | Initial Impedance (kOhm) | 90 sec. Impedance (kOhm) | Initial ½ cell Potential (mv) | 90 sec ½ cell potential (mv) | Notes | Surfactant Solution Resistivity (Ohm-meter) | Surface Tension (dynes/cm) |
|---|---|---|---|---|---|---|---|
| Dry | >550 | >550 | | | Failed | | |
| 29-14 TM/ T-Maz 20 | 58 | 80 | 120 | 120 | Climbing | 77.2 | 36.0 |
| 29-12 MT/ Maytein CT | 29 | 72 | 83 | 83 | Climbing | 2.2 | 26.7 |
| 29-11 MC/ Maytein C | 16 | 18 | 70 | 70 | Stable | 1.1 | 27.5 |
| 29-8 LS/ Lamepon S | 16 | 25 | 5 | 13 | Slight climb | 127.8 | 32.5 |
| 29-7 DS/ Dodecyl sulfate Na | 13 | 12.9 | 120 | 103 | Stable | 1.6 | 34.2 |
| 29-4 CC/ Chembetaine C | 27 | 36 | 110 | 91 | Stable | 1.7 | 34.3 |
| 29-3 AY/ Actrosal OY 75 | 25 | 29.8 | 100 | 83 | Stable | 1.9 | 32.7 |
| 29-1 AC/ Actrosol C75 | 16 | 28 | 46 | 35 | Slight climb | 1.1 | 34 |
| 10/20 gel | 18 | 25 | 40 | 40 | Slight climb | | |
| Saliva | 16 | >550 | 2 | | Failed | | |
| Ultrasonic | 33 | 34 | 109 | 106 | Stable | | |
| Elefix Gel | 39 | 28 | 33 | 36 | Declining | | |

EXAMPLE 7

Further Human Subject Tests

The tests were performed with a Nicolet AgCl electrode (019-417600), impedance meter, digital storage scope and digital voltmeter. A reference electrode and ground electrode were placed on the right side of the forehead and the shoulder respectively of a human subject. Standard skin abrasion and a 10/20 gel were used. The reference to ground measurements were verified throughout the test. Impedance was about 900 ohms and the half-cell potential was about 6–12 mV.

Table 2 shows the results for fifteen surfactant systems (5% solutions based on the active ingredients) and their penetration capabilities on polycarbonate membrane stacks.

A direct comparison was also made between the surfactant solutions and deionized water as shown. The 3ML-15638 emulsion was used at 80% activity, since it was considered to already be very dilute.

All tests of substances on the human subject were done on the forehead with no skin preparation. All test substances were injected using a syringe into a cup electrode secured to the forehead with medical tape. Second and third injections were done at five-minute intervals. A new site and electrode were used with each test. All Substances were tested. Testing began at 10:47 AM and was completed at 2:03 PM. The order shown below is not the order in which the substances were tested. All solutions used were standardized to 5% activity.

TABLE 7

Example 7 - Results for Substance Impedance (k$\Omega$)

| | Sample No. => | | | | | | | |
|---|---|---|---|---|---|---|---|---|
| | 29-1 AC Resist. (k$\Omega$) | 29-3 AY Resist (k$\Omega$) | 29-4 CC Resist (k$\Omega$) | 29-7 DS Resist (k$\Omega$ | 29-8 LS Resist (k$\Omega$) | 29-11 MC Resist (k$\Omega$) | 29-12 MT(2) Resist (k$\Omega$) | 29-14 TM Resist (k$\Omega$) |
| Dry | 34 | Off Scale | 140 | 132 | *** | 175 | 28 | 124 |
| 1st Injection Time (min) | | | | | | | | |
| 0 | 16 | 42 | 66.5 | 26 | 14(1) | 14 | 16 | 54 |
| 1 | 14 | 44 | 1305 | 22 | 13(1) | 12 | 22 | 41 |
| 2 | 12 | 54 | 11 | 20 | 13(1) | 14 | 25 | 39 |
| 3 | 12 | 59 | 10 | 20 | 13(1) | 14 | 29 | 39 |

TABLE 7-continued

Example 7 - Results for Substance Impedance (kΩ)

Sample No. =>

| | 29-1<br>AC<br>Resist.<br>(kΩ) | 29-3<br>AY<br>Resist<br>(kΩ) | 29-4<br>CC<br>Resist<br>(kΩ) | 29-7<br>DS<br>Resist<br>(kΩ | 29-8<br>LS<br>Resist<br>(kΩ) | 29-11<br>MC<br>Resist<br>(kΩ) | 29-12<br>MT(2)<br>Resist<br>(kΩ) | 29-14<br>TM<br>Resist<br>(kΩ) |
|---|---|---|---|---|---|---|---|---|
| 4 | 11 | 60 | 10 | 21 | 9 | 15 | 32 | 37 |
| 5 | 10 | 64 | 10 | 20 | 10 | 16 | 35 | 36 |
| 2nd Injection Time (min) | | | | | | | | |
| 0 | 10 | 26 | 9 | 15 | 5 | 8 | 9 | 33 |
| 1 | 9 | 27 | 8 | 15 | 6 | 9 | 10 | 31 |
| 2 | 8 | 29 | 8 | 15 | 6 | 9 | 10 | 30 |
| 3 | 8 | 31 | 8 | 15 | 6 | 10 | 12 | 30 |
| 4 | 7 | 32 | 8 | 15 | 6 | 10 | 13 | 30 |
| 5 | 7 | 35 | 8 | 14 | 6 | 11 | 13 | 30 |
| 3rd Injection Time (min) | | | | | | | | |
| 0 | 6 | 21 | 6 | 11 | 4 | 7 | 6 | 32 |
| 1 | 6 | 25 | 7 | 12 | 5 | 8 | 6 | 32 |
| 2 | 6 | 27 | 7 | 11 | 6 | 9 | 7 | 33 |
| Post Test(3) | Off Scale | 84 | —(4) | 11 | 8.4 | 55 | 13 | 88 |
| ½ cell Potential (mv) | 60–67 | 108–146 | 116–133 | −102 to −133 | −29 to +3 | −86 to −92 | −84 to −99 | 145–192 |
| Test 1 Impedance (kOhm) | 16–28 | 25–30 | 27–26 | 13 | 16–25 | 16–18 | 29–72 | 58–74 |
| Test 2 Impedance (kOhm) | 10–33 | | | 9–23 | 3–9 | 8–24 | | |

(1)The initial measurement was between the wire lead under test and reference and was corrected when discovered. The 13 kOhm readings correlated to 9.4 kOhm when the wiring was corrected.
(2)The lead physical attachment was a problem initially. This substance is sensitive to movement of the wire lead.
(3)Post Test measurement was performed after the completion of all the tests. Substance 29-8 LS retained a low impedance almost one hour after its initial test. Substance 29-8 LS was a Lamepon S formulation from first lot (327961).
(4)Measurement not taken.

Substances 29-1 AC, 29-4 CC, and 29-8 LS gave the best results. Substance 29-8 LS, Lamepon S, gave the best Test 2 Impedance result. Substances 29-3 AY and 29-14 TM had the worst results and accordingly are deleted from further consideration by this test.

EXAMPLE 8

Human Subject Test Results

The tests were performed with a Nicolet AgCl electrode (019-417600), impedance meter, digital storage scope and digital voltmeter. A reference electrode and ground electrode were placed on the right side of the forehead and the shoulder respectively. Standard abrasion and 10/20 gel were used. The reference to ground measurements were verified throughout the test. Impedance was 900 ohms and the half-cell potential was 6–12 mV. All tests were done on the forehead with no skin preparation. All test substances were injected using a syringe into a cup electrode secured to the forehead with medical tape. Second and third injections were done at five-minute intervals. A new site and electrode were used with each test. Only substances 29-1 AY, 29-7 DS, 29-8 LS, and 29-11 MT, identified above were used in this test.

TABLE 8

Example 8 Results - Substance Impedance (kOhm)

| Time (min) ⇓ | 29-1 AC | 29-7 DS | 29-8 LS | 29-11 MC |
|---|---|---|---|---|
| Dry Initial Inject. | Off Scale | 137 | Off Scale | 140 |
| 0 | 30.4 | 33 | 40 | 32.0 |
| 1 | 30.7 | 23.3 | 10.3 | 24.5 |
| 2 | —(2) | 22.2 | 10.3 | 22.5 |
| 3 | 30.6 | 22.0 | 10.3 | 21.4 |
| 4 | 32.2 | 21.8 | 10.3 | 21.7 |
| 5 | 32.8 | 21.5 | 10.5 | 22.7 |
| Second Inject | | | | |
| 0 | 16.0 | 12.5 | 5 | 13.5 |
| 1 | —(2) | 12.0 | 5.7 | 17.7 |
| 2 | 18.2 | 11.5 | 5.9 | 19.1 |
| 3 | —(2) | 11.2 | 6.1 | 21.4 |
| 4 | —(2) | 11.6 | 6.1 | 23.0 |
| 5 | 20.2 | 12.5 | 6.0 | 25.1 |
| Third Inject | | | | |
| 0 | 10.0 | 8.6 | 3.2 | 7.5 |
| 1 | 13.8 | 13.7 | 3.9 | 7.8 |
| 2 | 14.4 | 14.2 | 4.1 | 11.2 |

TABLE 8-continued

Example 8 Results - Substance Impedance (kOhm)

| Time (min) ⇓ | 29-1 AC | 29-7 DS | 29-8 LS | 29-11 MC |
|---|---|---|---|---|
| Post Test(1) | 70.0 | —(2) | 6.1 | —(2) |
| ½ Cell Potential (mv) | 44–57 | 96–135 | 2–13 | 71–82 |
| Previous Test Impedance (kOhm) | 19–28 | 12–13 | 16–25 | 16–18 |

(1)Post Test measurement was performed after the completion of the next set of electrode tests. The measurement was generally made about 17–20 minutes after the first test.
(2)Measurement not taken.

The substances all improved with additional injections. The rising impedance seen in the last test was reduced. Although not wishing to be constrained by theory, this effect may be explained by evaporation. Substance 29-8 LS, which is Lamepon S™, showed the best results in terms of resistance. No adverse skin reactions were found with any of the substances.

EXAMPLE 9

Tests for surfactant solution electrical conductivity were performed on additional solutions including solutions having different activities and various excipients. These solutions were then used for additional human subject tests described further below.

Excipients such as polyethylene glycol 200 (PEG 200), NaCl, citric acid, and combinations of PEG 200 and NaCl were added to some of the basic surfactant solutions. In addition, the surfactant solutions had varied amounts of activity as shown in Table 9 below. The important results shown in this table are that increasing concentrations (% activity) of Actrosol C75, Lamepon S™, MayTein C™, and MayTein CT™ resulted in lower resistivity in the surfactant solution.

TABLE 9

Surfactant Solution Conductivity Data

| Date Prepared L g Bo k Ref. # | Formulation | Surfactant % Active | Excipient | Surfactant Solution (vwr) Conductivity mS/cm | Solution Resistivity Ohm-Meter |
|---|---|---|---|---|---|
| 42-01 AC | Actrosol C75 | 20 | None | 38.2 | 0.2618 |
| 42-02 AC | Actrosol C75 | 30 | None | 60.5 | 0.1653 |
| 42-03 CC | Chembetaine C ™ | 20 | None | 21.4 | 0.4673 |
| 42 04 CC | Chembetaine C ™ | 30 | None | 12.9 | 0.7776 |
| 42-05 DS | Dodecyl Sulfate, Na salt | 5 | 0.1% PEG 200 | 5.9 | 1.6978 |
| 42-06 DS | Dodecyl Sulfate, Na salt | 5 | 0.01% NaCl | 6.2 | 1.6129 |
| 42-7 DS | Dodecyl Sulfate, Na salt | 5 | 0.01% Citric acid | 6.0 | 1.6611 |
| 42-08 DS | Dodecyl Sulfate, Na salt | 5 | 0.1% PEG 200, 0.01 % NaCl | 6.2 | 1.6234 |
| 42-09 DS | Dodecyl Sulfate, Na salt | 20 | None | 41.0 | 0.2439 |
| 42-10 DS | Dodecyl Sulfate, Na salt | 30 | None | 66.2 | 0.1511 |
| 42-11 LS | Lamepon S ™* | 5 | 0.1% PEG 200 | 78.0 | 0.1282 |
| 42-12 LS | Lamepon S ™* | 5 | 0.01% NaCl | 77.3 | 0.1294 |
| 42-13 LS | Lamepon S ™* | 5 | 0.01% Citric acid | 76.4 | 0.1309 |
| 42-14 LS | Lamepon S ™* | 5 | 0.1% PEG 200, 0.01 % NaCl | 77.4 | 0.1292 |
| 42-15 LS | Lamepon S ™* | 20 | None | 223.0 | 0.0448 |
| 42-16 LS | Lamepon S ™* (viscous) | 30 | None | 142.5 | 0.0702 |
| 42-17 MC | MayTein C ™ | 20 | None | 45.0 | 0.2222 |
| 42-18 MC | MayTein C ™ | 30 | None | 66.0 | 0.1515 |

TABLE 9-continued

Surfactant Solution Conductivity Data

| Date Prepared L g Bo k Ref. # | Formulation | Surfactant % Active | Excipient | Surfactant Solution (vwr) Conductivity mS/cm | Solution Resistivity Ohm-Meter |
|---|---|---|---|---|---|
| 42-19 MT | MayTein CT ™ | 20 | None | 15.7 | 0.6382 |
| 42-20 MT | MayTein CT ™ | 30 | None | 18.0 | 0.5571 |

Note:
All Lamepon S-based formulations with an * were prepared from first lot number (327961)

EXAMPLE 10

Test performed with Nicolet AgCl electrode (019-417600), impedance meter, and digital voltmeter. A reference electrode and ground electrode were placed on the left side of the forehead and the shoulder of a human subject respectively. Standard abrasion and 10/20 gel were used. The reference to ground measurements were verified throughout the test. Impedance and the half-cell potential of the reference electrode were recorded and are listed in the results below. All tests substances were injected using a syringe into a cup electrode secured to the forehead with medical tape. Second and third injections were done at five-minute intervals. A new site and electrode were used with each test. The substances were tested in pairs. All Substances were tested. The impedance meter was wired to remain on as it was in previous tests.

The substances from Table 9 were used to obtain the data listed in Table 10.

TABLE 10

Example 10 Resistivity Resistivity Results
(kOhm - unless identified otherwise)

| | 42-1 AC | 42-2 AC | 42-3 CC | 42-4 CC | 42-17 MC | 42-18 MC | 42-5 DS* | 42-6 DS* | 42-7 DS** | 42-8 DS** | 42-9 DS* | 42-10 DS* | 42-11 LS | 42-12 LS | 42-13 LS | 42-14 LS | 42-15 LS* | 42-16 LS* | 42-19 MT | 42-20 MT |
|---|---|---|---|---|---|---|---|---|---|---|---|---|---|---|---|---|---|---|---|---|
| REF Dry | 0.9 | 1.0 | 0.9 | 1.0 | 0.9 | 1.0 | 1.5 | 1.5 | 1.4 | 1.4 | 1.3 | 1.4 | 1.5 | 1.5 | 1.4 | 72 | 1.4 | 1.4 | 1.4 | 1.4 |
| | Off Scale | Off Scale | 162 | Off Scale | 173 | Off Scale | 94 | 48 | 52 | 48 | 45 | 155 | 26 | 18 | 92 | 1.4 | 129 | 20 | Off (5) Scale | 102 |
| Time (min) ⇓ | | | | | | | | | | | | | | | | | | | | |
| 1st Injection | 10 | 10 | 50 | 23 | 23 | 35 | 18 | 8.4 | 8.7 | 3.8 | 7.4 | 26 | 1.5 | 3.1 | 6.2 | 8.7 | 7.8 | 4.5 | 10 | 9 |
| 1 | | | | 11.6 | 11.5 | 18 | 12.6 | 6.8 | 8 | 4.5 | 3.8 | 12.2 | 1.5 | 2 | 2.3 | 6.8 | 2 | 1.3 | | 6.3 |
| 2 | 7 | 10 | 25 | 8.5 | 13 | 13.6 | 13 | 6 | 8 | 4.3 | 3.8 | 9.5 | 1.5 | 1.8 | 2.3 | 7.6 | 2 | 1 | 11 | 5.3 |
| 3 | | | 20 | | 13.2 | 11.8 | 13.5 | 6 | 8 | 4.2 | 3.7 | 8.2 | 1.5 | 1.5 | 2.2 | 8 | 1.9 | 0.9 | 10 | 9 |
| 4 | 6.5 | | 19 | 6 | 13.5 | 10.8 | 12.8 | 5.2 | 7.8 | 5 | 3.7 | 6.8 | 1.5 | 1.5 | 2.2 | 7.5 | 1.8 | 0.9 | 11.5 | 10.7 |
| 5 | 5.8 | 8.5 | 18 | 5.2 | 13 | 10 | 13.5 | 5.2 | 5.2 (1) | 5.8 | 3.5 | 5.5 | 1.5 | 1.5 | 2.3 | 7.2 | 1.8 | 0.9 | 13.8 | 12.5 |
| Time (min) ⇓ | | | | | | | | | | | | | | | | | | | | |
| 2nd Injection | 3.7 | 8 | 13 | 3.5 (1) | 6 | 5.5 | 6.5 | 3.3 | 5.8 | 1.9 (1) | 2.1 | 4.1 | 0.8 | 1 | 1.1 | 2.6 | 1.6 | 0.9 | 3.6 | 5.2 (7) |
| 1 | | 8 | | 3 | 6.8 | 5.5 | 8 | 4.5 | 6 | 2.7 | 2 | 3.3 | 1 | 1.3 | 2 | 5 | 1.5 | 0.8 | 5 | 6 |
| 2 | 3.5 | 7.9 | 11.3 | 3.5 | 7.8 | 5.5 | 8.5 | 4.5 | 5.9 | 2.7 | 2 | 2.6 | 1.3 | 1.4 | 2.3 | 5.3 | 1.4 | 0.9 | 5 | 7.9 |
| 3 | 4 | 7.8 | 11.7 | 3.9 | 8 | 5.5 | 9 | 4.2 | 5.8 | 3.2 | 1.8 | 2.8 | 1.3 | 1.4 | 2.3 | 5.3 | 1.7 | 0.9 | 5 | 8.9 |
| 4 | 3.8 | 7.8 | 11.8 | 4.0 | 8.5 | 5.8 | 8.7 | 3.8 | 2.5 (2) | 2.5 | 1.6 | 2.6 | 1.2 | 1.5 | 2.4 | 5.3 | 1.8 | 0.8 | 5 | 5.5 (7) |
| 5 | 4 | 7 | 7(1) | | 8.5 | 5.8 | 7.8 | 3.7 | 2.5 (2) | 2.5 | 1.7 | 2.7 | 1.3 | 1.4 | 3.3 | 4.3 | 1.9 | 0.8 | 3(6) | 5.8 |
| Time (min) ⇓ | | | | | | | | | | | | | | | | | | | | |
| 3rd Injection | 3 | 4.5 | 5.5 | 3 | 4 | 3.5 | 4.2 | 2.6 | —(3) | —(3) | 0.9 | 1.8 | 0.7 | 0.9 | 0.9 | 2.7 | —(4) | —(4) | 2.1 | 3.4 |
| 1 | | 4 | 5 | | 3.2 | 4.8 | 4 | 4.5 | 2.8 | — | — | 1.7 | 1.7 | 1.1 | 1.3 | 1.3 | 3.8 | — | — | 2.6 | 3.4 |
| 2 | | 3.8 | 6 | 6.6 | 3 | 4.8 | 4 | 4 | 2.8 | — | — | 1.7 | 1.7 | 1.2 | 1.3 | 1.4 | 3.8 | — | — | 2.9 | 3.2 |
| 3 | | 4 | | | | | | | | | | | | | | | | 2 | 1 | | |

TABLE 10-continued

Example 10 Resistivity Resistivity Results
(kOhm - unless identified otherwise)

| | 42-1 AC | 42-2 AC | 42-3 CC | 42-4 CC | 42-17 MC | 42-18 MC | 42-5 DS* | 42-6 DS* | 42-7 DS** | 42-8 DS** | 42-9 DS* | 42-10 DS* | 42-11 LS | 42-12 LS | 42-13 LS | 42-14 LS | 42-15 LS* | 42-16 LS* | 42-19 MT | 42-20 MT |
|---|---|---|---|---|---|---|---|---|---|---|---|---|---|---|---|---|---|---|---|---|
| Post Test | 14.4 (70 min) | 12.7 (70 min) | | | | | | | | | | | 9.8 (25 min) | 1.7 (25 min) | | | 2.7 (35 min) | 0.9 (35 min) | | |
| ½ cell Potential (mv) | 4 to 19 | −20 to −7 | 65 to 72 | 39 to 62 | 22 to 34 | −4 to 16 | 55 to 106 | 71 to 120 | 66 to 109 | 77 to 101 | 51 to 74 | 85 to 106 | 12 to 17 | 18 to 21 | 9 to 11 | −1 to −22 | −34 to −37 | −32 to −46 | 20 to 36 | 14 to 29 |

Notes for Table 10
*Slight Skin Irritation
**Skin Irritation
(1)Holding the electrode lowered the impedance. Several of the substances were soapy in nature and loosened the tape quickly.
(2)Repositioned fingers
(3)No third injection was given because of irritation.
(4)No third injection was needed. (Good electrical conductivity that was not improving)
(5)The initial dry site impedance was 6 kOhm. A new site and electrode were selected. Although the electrode site was about two inches away and was above the initial solution test sites, a residual effect may have been the cause.
(6)Holding the electrode lowered the impedance.
(7)Loose electrode
(8)All substances were tested for impedance. Readings in the table are all in kOhm except the ½ cell potential which is in (mv).

The Lamepon S™ appeared to be the best substance. Additives did not enhance its performance.

The PRG 200 may reduce the performance of the Lamepon S™. Increasing concentration did not necessarily improve the performance of all the surfactants, although the 30% concentration was better in the Chembetaine C™ and Lamepon S™.

Method for Examples 11 through 16

Additional solutions illustrated in Examples 11 to 16 below were tested as follows. Tests were performed with a Nicolet AgCl electrode (Part No. 019-417600), impedance meter, and digital voltmeter. A reference electrode and ground electrode were placed on the left side of a subject's forehead and the subjects shoulder respectively. Standard abrasion and 10/20 gel were used. The reference to ground measurements were verified throughout the test. Impedance and the half-cell potential of the reference electrode were recorded and are listed in the results below. All tests of the substances were done on the subject's forehead with no skin preparation (e.g. no mechanical abrasion or chemical preparation). All test substances were swabbed on the subjects head with a previously dry Q-tip. A cup electrode was secured to the subject's forehead with essentially non-conducting medical tape. A new forehead site and electrode were used with each test. The impedance meter was wired to remain on as it was in previous tests.

EXAMPLE 11

Gelling agents were added to Lamepon S™ and one sample of Dodecyl Sulfate as shown in Table 11.

TABLE 11

| | Gelling Agents | |
|---|---|---|
| Substance Sample No. | Surfactant | Gelling Agent (% by weight) |
| A-LS | Lamepon S[a] | NONE |
| B-LS | Lamepon S[b] | NONE |

TABLE 11-continued

| | Gelling Agents | |
|---|---|---|
| Substance Sample No. | Surfactant | Gelling Agent (% by weight) |
| C-LS | Lamepon S[a] | 3.2% Silver Microspheres |
| D-LS | Lamepon S[a] | 3.6% Carbopol EZ-2 |
| E-LS | Lamepon S[a] | 1.0% Carbopol EZ-2 |
| F-LS | Lamepon S[a] | 1.0% Cellosize QP300 |
| G-LS | Lamepon S[a] | 1.0% Natrosol 250 LR (HEC) |
| H-LS | Lamepon S[a] | 0.5% PVP K90 |
| I-LS | Lamepon S[b] 5% active | NONE |
| J-LS | Lamepon S[a] 5% active | 0.1% PEG 200 |
| K-LS | Lamepon S[b] 20% active | NONE |
| L-DS | Dodecyl Sulfate, Na salt 5% | 0.1% PEG 200 0.01% NaCl |

[a]Lamepon S ™ solution prepared from second lot - 30.4% active
[b]Lamepon S ™ solution prepared from first lot - 52.7% active.

EXAMPLE 12

Table 12 illustrates impedance measurements as outlined above for test subject A1. The electrodes were attached to the subject as described above. The reference impedance was 1.5 to 1.8 kOhms.

TABLE 12

| | Impedance Measurements (Subject A) | | |
|---|---|---|---|
| Sample No. | Impedance (kOhm) | ½ Cell Potential (mv) | ½ Cell Standard Deviation |
| A-LS | 8.6 | −8.04 | 7.02 |
| B-LS | 11.9 | 58.16 | 2.27 |

TABLE 12-continued

Impedance Measurements (Subject A)

| Sample No. | Impedance (kOhm) | ½ Cell Potential (mv) | ½ Cell Standard Deviation |
|---|---|---|---|
| C-LS | 12.9 | −4.20 | 6.29 |
| D-LS | 12.5 | 5.88 | 1.37 |
| E-LS | 12.6 | 0.86 | 4.04 |
| F-LS | 9.6 | −1.86 | 6.51 |
| G-LS | 8.6 | 6.24 | 4.46 |
| H-LS | 17.6 | 4.58 | 2.62 |

The values for impedance reported in Table 12 represent the lowest values obtained nominally after 6–7 minutes of testing. The results from Table 12 show that the new lot of Lamepon S™ gelled with 1% Cellosize QP300 and 1% Natrosol 250LR (HEC). Samples F and G respectively gave impedance results similar to the new lot ungelled Lamepon S™ of Sample A. Thus gelation with these gelling agents did not appear to affect impedance. An additional observation from this table is that Samples A and B show that as the concentration of Lamepon increases above about 30% to about 53% the impedance begins to increase.

EXAMPLE 13

Table 13 illustrates impedance measurements as outlined above for test subject B1. Half-cell potentials were measured and half-cell standard deviations calculated. The electrodes were attached to the subject as described above. The test compares ungelled solutions of surfactant with gelled solutions. The reference impedance was 1.5 to 2.1 kOhms.

TABLE 13

Impedance Measurements (Subject B1)

| Sample No. | % Activity | Impedance (kOhm) | ½ Cell Potential (mv) | ½ Cell Standard Deviation |
|---|---|---|---|---|
| L-DS | 5 | 9.2 | 92.54 | 4.70 |
| F-LS | 30.4 | 7.3 | −1.21 | 2.26 |
| J-LS | 5 | 8.0 | 1.0 | 3.68 |
| G-LS | 30.4 | 12.2 | 2.40 | 7.15 |

Tests reported in Table 13 were side by side tests of Sample L-DS which was a 5% active solution gelled with 0.1% PEG 200 and 0.1% NaCl, and Sample F-LS material which was 30.4% active Lamepon S™ gelled with 1% Cellosize QP300. A second side by side test was also made for Sample J-LS which was a 5% active solution of Lamepon S™ gelled with 0.1% PEG 200 and Sample G-LS which was a 30.4% active solution of Lamepon S™ gelled with 1% Natrosol 250 LR (HEC).

The results also show that the gelled Lamepon S™ of high activity outperformed the gelled Dodecyl Sulfate of low activity. This is important because Samples 42-10DS and 42-9DS of Table 9 indicated improvement in impedance as the activity of dodecyl sulfate was reduced. The results for Table 13 thus indicate that Lamepon S™ will outperform dodecyl sulfate at both high and low concentrations.

EXAMPLE 14

Table 14 illustrates additional impedance measurements as outlined above for test subject B1. Half-cell potentials were measured and half-cell standard deviations calculated. The electrodes were attached to the subject as described above. The test compares gelled solutions for several surfactant solutions. The reference impedance was 1.7 to 2.0 kOhms. This example illustrates impedance tests for several combinations of surfactants and gelling agents.

Results indicate that adding PEG as a gellant resulted in a low initial impedance that increased over time for both dodecyl sulfate and Lamepon S™ (Samples L-DS and J-LS. Lamepon S™ gelled with 1% Cellusize QP300 or 1% Natrosol 250 LR(HEC) did not exhibit this phenomena but remained stable. When the materials gelled with PEG were mixed with Lamepon S™ gelled with the Cellusize or the Natrosol the instability in the form of a steady rise in impedance was reduced to a slight rise. This indicates that PEG is not a preferred gellant while Natrosol and Cellusize are.

TABLE 14

Additional Impedance Measurements (Subject B1)

| Sample No. | Impedance (kOhm) | ½ Cell Potential (mv) | ½ Cell Standard Deviation |
|---|---|---|---|
| L-DS | 11* | 94.34 | 12.71 |
| L-DS & F-LS | 5.7** | 9.97 | 4.75 |
| F-LS | 5.9 | 7.40 | 3.28 |
| J-LS | 26.7* | −9.67 | 14.91 |
| J-LS & G-LS | 10.0** | 4.57 | 10.50 |
| G-LS | 9.1 | 3.83 | 3.55 |

Reference: 1.7 to 2.0 kΩ
*Initial reading was the lowest impedance with a steady rise over the course of the test.
**One minute reading was the lowest impedance with a slight rise over the course of the test.

EXAMPLE 15

Table 15 illustrates further impedance measurements as outlined above for test subject B1. Half-cell potentials were measured and half-cell standard deviations calculated. The electrodes were attached to the subject as described above. The example illustrates three ungelled solutions of Lamepon S™ surfactant and one Lamepon S™ gelled solution. A minimum impedance was found at about 20% activity for ungelled Lamepon S™. Addition of 1.0% Natrosol 250 LR (HEC) to the highest (30.4% active) Lamepon S™ resulted in reduced impedance. It would thus be generally expected that addition of this type of gelling agent will besides other effects also enhance impedance. The reference impedance was about 2.4 kOhms.

TABLE 15

Further Impedance Measurements (Subject B1)

| Sample No. | % Activity | Impedance (kOhm) | ½ Cell Potential (mV) | ½ Cell Standard Deviation |
|---|---|---|---|---|
| I-LS | 5 | 5.9* | 18.61 | 5.93 |
| K-LS | 20 | 2.7* | −22.65 | 2.24 |
| A-LS | 30.4 | 8.7 | 3.47 | 4.63 |
| G-LS | 30.4 | 7.3 | 10.96 | 3.69 |

Reference 2.4 kΩ
*A second injection was done on the thin solutions at 10 minutes.

EXAMPLE 16

Table 16 illustrates yet additional impedance measurements as outlined above for test subject C1. Half-cell potentials were measured and half-cell standard deviations calculated. The electrodes were attached to the subject as described above. The example was essentially a repeat of Example 15, except that a different test subject was used. As before a minimum impedance was again measured with Lamepon S™ at an activity level of about 20%. This time, however, the addition of 1.0% Natrosol 250 LR (HEC) to the Lamepon S™ with highest activity (30.4% active) resulted in increased impedance. This is perhaps best explained as an anomaly, since for this sample the ½ cell Standard Deviation was much larger than the ½ cell potential. The reference impedance was about 2.4 kOhms.

TABLE 16

Impedance Measurements (Subject C1)

| Sample No. | % Activity | Impedance (kOhm) | ½ Cell Potential (mV) | ½ Cell Standard Deviation |
|---|---|---|---|---|
| I-LS | 5 | 10.2 | 13.51 | 9.48 |
| K-LS | 20 | 3.6 | −24.86 | 5.53 |
| A-LS | 30.4 | 4.8 | 3.43 | 5.91 |
| G-LS | 30.4 | 7.0 | 6.51 | 9.65 |

Reference 2.4 kΩ

Drug Delivery

Another embodiment of the invention includes the use of the surfactants disclosed herein to enhance the delivery of drug compounds through the skin or membranes. The surfactant acts as a carrier for drugs having small molecules, drugs with large molecules including proteins and other biologics. The embodiment covers the promotion of small or large molecule drug compounds through the skin. The transport of the drugs could be aided by an electrical potential. Typically, the drugs are used alone or are attached to carrier molecules that can be charged with an electrical bias so as to enhance the transport of the molecules.

The transport enhancing material can be used on or in a patch for enhanced delivery/transport of drugs or other compounds; and an additive to topical creams or gels with drug compounds mixed into the gel.

Non-Invasive Diagnostics

Another embodiment of the invention includes the use of the materials herein as enhancers for non-invasive diagnostic methods. As has been discussed in earlier sections above, the surfactants of the invention have been demonstrated to increase electrical conductivity across the skin. These surfactants are also beneficial in promoting the uptake, diffusion, and capture of interstitial fluids through the skin. The interstitial fluids can carry proteins, biochemicals and other molecules from the body that are indicative of a disease state, physiological condition, or response to a pharmaceutical or other therapy.

As an example, the surfactants of the invention can be embodied in a band-aid that is attached to the skin and draws out interstitial fluid that carries out the analyte of interest. Such analytes may include, but are not limited to, insulin, antibodies developed by the immune system in response to infectious diseases such as strep infections, anthrax, hepatitis, and so on, or biomolecules that indicate response to a drug such as clotting factors or absorption of the drug in appropriate amounts. The surfactant/band-aid type diagnostic system could include immuno-chromatographic assays that change color and give a visible measurement to the patient or health care provider about the physiological system.

Figure 4:
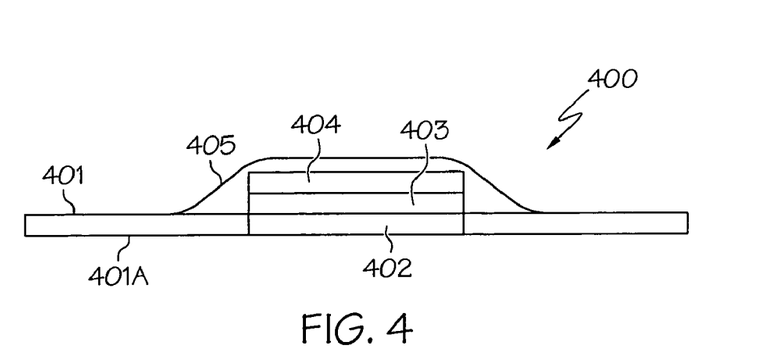
FIG. 4 is a schematic drawing of a multilayer patch according to the invention.

FIG. 4 illustrates a noninvasive diagnostic patch 400 that can be used to monitor bodily functions. The patch 400 consists of holding material 401 that may be adhesive 401A at the bottom thereof where it contacts the skin. A first layer 402 containing the materials disclosed in this invention is located to be in proximity to the skin. A second reactive layer 403 is located above the first layer and contains chemicals that are reactive with materials extracted from the body through the skin. A third layer 404 contains indicators visible to a user. Enveloping protective layer 405 is optional and may be clear or have a clear window so that the indicators are visible to the user.

A patch similar to that disclosed in FIG. 4 may be used to deliver chemicals, drugs or medicine to a patient. In that case, layer 404 is not needed and only a drug containing layer 403 and a layer 402 containing the materials according to the present invention are needed. In some embodiments the chemicals, drugs or medications may be mixed into the materials of the present invention, in which case only layer 402 would be needed.

Electrosurgery

In electrosurgery, large patch electrodes are used to establish a return path for monopolar surgery tools. If the patch electrodes do not make sufficiently good contact with the patient's skin, the surgery may be less effective and, much worse, the patient may receive severe burns at the return electrode from the heat generated due to the higher contact resistance at the return electrode.

Currently, the gels applied to electrosurgery return electrodes contain highly ionic compounds. Addition of a surfactant such as those identified herein should have at least two benefits. First, the surfactant will drive the ions through the skin faster than if the ionic compounds are used in the absence of the surfactant. This will permit use of the electrodes more quickly after their application to the patient. The second benefit is that it should be possible to increase the amount of ions present in the skin layer, thus reducing the contact resistance between the electrode and the skin. This would further reduce the risk of burns and improve the performance of the surgical procedure. Important aspects of the invention herein include the use of the surfactant to improve ionic penetration of the skin and the specific properties of the surfactant mixtures that optimize its performance specifically for skin.

Figure 5:
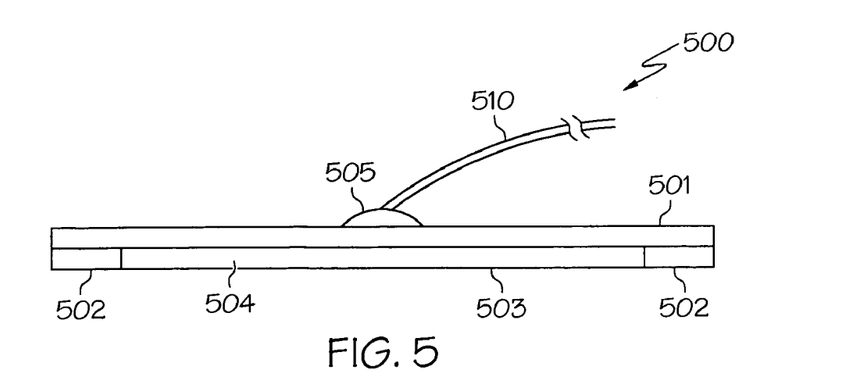
FIG. 5 is a schematic drawing of an electrosurgery electrode according to the invention.

Referring now to FIG. 5, this figure illustrates a schematic side view of a typical electrosurgery patch 500. A metallic conductive material 501 typically provides the support for the patch 500. Around the outside of the bottom 503 of the patch, an adhesive strip 502 typically surrounds the patch perimeter. Conductive material 504 typified by the conductive materials of the invention are placed inside this area. The conductive material may be in a matrix material or may be applied as a gel that adheres to the electrode conductor 501. Typically a connector 505 is found on the upper surface of the electrosurgery electrode for connection to the source of power by a wire 510.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. An electrode providing electrical contact with a surface of a patient, said electrode comprising:
   A. a conductive member; and
   B. a conduction enhancer in contact with said conductive member, said conduction enhancer comprising a carrier and a lipopolypeptide.

2. The electrode according to claim 1, wherein said lipopolypeptide comprises an acyl peptide.

3. The electrode according to claim 2, wherein said acyl peptide comprises an acylated polypeptide salt.

4. The electrode according to claim 3, wherein said carrier and conduction enhancer provide electrical contact with an electrical resistivity comprising less than about 10K Ohms when said electrode is applied to said patient's surface.

5. The electrode according to claim 4, wherein said carrier comprises a liquid, cream, or gel.

6. The electrode according to claim 1, wherein said conduction enhancer has an activity between about 0.25% and about 60%.

7. The electrode according to claim 1, wherein said conduction enhancer has an activity between about 4% and about 50%.

8. The electrode according to claim 1, wherein said conduction enhancer has an activity between about 5% and about 30%.

9. The electrode according to claim 1, wherein said conduction enhancer has an activity between about 10% and about 30%.

10. The electrode according to claim 1, wherein said carrier comprises a liquid, cream, or gel.

11. A method for decreasing the electrical resistivity between an electrode and the surface of a patient comprising: placing a carrier and a conduction enhancer comprising a lipopolypeptide between said electrode and said surface.

12. The method according to claim 11, wherein said lipopolypeptide comprises an acyl peptide.

13. The method according to claim 12, wherein said acyl peptide comprises an acylated polypeptide salt.

14. The method according to claim 13, wherein said carrier and conduction enhancer provide electrical contact with an electrical resistivity comprising less than about 10K Ohms when said electrode is applied to said patient's surface.

15. The method according to claim 14, wherein said electrical resistivity is obtained in about 0.001 seconds to about 3 minutes.

16. The method according to claim 14, wherein said electrical resistivity is obtained within about 0.01 seconds to about 30 seconds.

17. The method according to claim 14, wherein said electrical resistivity is less than about 6K Ohms.

18. The method according to claim 14, wherein said electrical resistivity is maintained for at least about 8 hours.

19. The method according to claim 14, wherein said electrical resistivity is maintained for at least about 72 hours.

20. The method according to claim 14, wherein said carrier comprises a liquid, cream, or gel.

21. The method according to claim 11, wherein said carrier and conduction enhancer comprise a gelling agent.

22. The method according to claim 11, wherein said carrier comprises a liquid, cream, or gel.

23. An electrode providing electrical contact with a surface of a patient, said electrode comprising:
   A. a conductive member; and
   B. a conduction enhancer in contact with said conductive member comprising a carrier and a surfactant represented by the formula:

$$R'-CO-NH\{CR''H-CO-NH-CRH\}_n COOM$$

wherein R, R', and R" are the same or different and may be independently selected from the group consisting of alkyl, aryl, amine, carbonyl, and carboxyl moieties; R, and R" may also be independently selected from the group consisting of —H, and —SH;
   wherein the repeat unit, n, is an integer from about 2 to about 2000; and wherein M is a metal ion.

24. The electrode according to claim 23, wherein when a carbon containing moiety is selected, R, R', and R" have 1–20 carbon atoms.

25. The electrode according to claim 23, wherein said repeat unit, n, is an integer from about 150 to about 1800.

26. The electrode according to claim 23, wherein said surfactant is a mixture of compounds selected from said formula.

27. The electrode according to claim 23, wherein said metal ion, M, is selected from the group consisting of $K^+$, $Na^+$, and mixtures thereof.

28. The electrode according to claim 23, wherein said carrier comprises a liquid, cream, or gel.

29. A method for making electrical contact between an electrode and a patient's surface, which comprises the step of applying an electrode having a surface coated with a mixture of a carrier and a conduction enhancer comprising a lipopolypeptide.

30. The method according to claim 29, wherein said lipopolypeptide comprises an acyl peptide.

31. The method according to claim 30, wherein said acyl peptide comprises an acylated polypeptide salt.

32. The method according to claim 31, wherein said carrier and conduction enhancer provide electrical contact with an electrical resistivity comprising less than about 10K Ohms when said electrode is applied to said patient's surface.

33. The method according to claim 32, wherein said acyl peptide has an activity of at least 0.25%.

34. The method according to claim 32, wherein said electrical resistivity is obtained in about 0.001 seconds to about 3 minutes.

35. The method according to claim 32, wherein said electrical resistivity is obtained within about 0.01 seconds to about 30 seconds.

36. The method according to claim 32, wherein said electrical resistivity is less than about 6K Ohms.

37. The method according to claim 32, wherein said electrical resistivity is maintained for at least about 8 hours.

38. The method according to claim 32, wherein said carrier comprises a liquid, cream, or gel.

39. The method according to claim 29, wherein said patient's surface is unabraded.

40. The method according to claim 29, wherein said mixture comprises a gelling agent.

41. The method according to claim 29, wherein said carrier comprises a liquid, cream, or gel.

42. A surgical electrode for electrosurgery comprising a conductor and a conduction-enhancing amount of an acyl peptide.

43. An electrode for electrosurgery in a patient comprising:
 a. a conductor; and
 b. a conduction-enhancing amount of a mixture of a carrier and an acylated polypeptide salt, wherein said mixture is applied to a surface of said conductor.

44. The electrode according to claim 43, wherein said conduction enhancer has an activity between about 0.25% and about 60%.

45. The electrode according to claim 43, wherein said conduction enhancer has an activity between about 4% and about 50%.

46. The electrode according to claim 43, wherein said conduction enhancer has an activity between about 5% and about 30%.

47. The electrode according to claim 43, wherein said conduction enhancer has an activity between about 10% and about 30%.

48. The electrode according to claim 43, wherein said carrier comprises a liquid, cream, or gel.

* * * * *

UNITED STATES PATENT AND TRADEMARK OFFICE
CERTIFICATE OF CORRECTION

PATENT NO. : 7,099,713 B2
APPLICATION NO. : 10/608579
DATED : August 29, 2006
INVENTOR(S) : Browning et al.

It is certified that error appears in the above-identified patent and that said Letters Patent is hereby corrected as shown below:

Column 6, Line 41, ".01." should be -- .01 --

Column 11, Lines 45, 46, 47 (starting at "Table 2" through "membrane stacks.")
-- Delete --

Column 12, Lines 33, 34, 35 (starting at "A direct" through "very dilute.") -- Delete --

(amendment submitted listed wrong page and line number for correction)
    (amendment did not request insertion of text at this point)

Column 13, Table 7, "108-146" should be -- 108-143 --

Column 22, Line 10, "(Samples L-DS and J-LS." should be -- (Samples L-DS and J-LS)--.

Signed and Sealed this

Tenth Day of April, 2007

JON W. DUDAS
*Director of the United States Patent and Trademark Office*